(12) United States Patent
Leibitzki et al.

(10) Patent No.: US 9,168,345 B2
(45) Date of Patent: Oct. 27, 2015

(54) BREATHING DEVICE COMPRISING A SUPPORT FOR SPEECH VALVES AND/OR HEAT AND MOISTURE EXCHANGE DEVICES WITHOUT FIXING TO THE CANNULA

(75) Inventors: Harry Leibitzki, Blankenburg (DE); Steffen Suess, Halberstadt (DE)

(73) Assignee: Primed Halberstadt Medizintechnik GMBH, Halberstadt (DE)

( * ) Notice: Subject to any disclaimer, the term of this patent is extended or adjusted under 35 U.S.C. 154(b) by 297 days.

(21) Appl. No.: 13/878,614

(22) PCT Filed: Sep. 28, 2011

(86) PCT No.: PCT/DE2011/001808
§ 371 (c)(1),
(2), (4) Date: Apr. 12, 2013

(87) PCT Pub. No.: WO2012/048682
PCT Pub. Date: Apr. 19, 2012

(65) Prior Publication Data
US 2013/0192603 A1  Aug. 1, 2013

(51) Int. Cl.
*A61M 16/04* (2006.01)
*A61M 16/10* (2006.01)

(52) U.S. Cl.
CPC ......... *A61M 16/047* (2013.01); *A61M 16/0468* (2013.01); *A61M 16/1045* (2013.01)

(58) Field of Classification Search
CPC ........... A61F 2/20; A61F 2/203; A61F 5/441; A61F 5/445; A61F 5/448; A61M 11/00; A61M 16/00; A61M 16/04; A61M 16/0468; A61M 16/047; A61M 16/10; A61M 16/1045; A61M 16/20; A62B 9/02; B32B 37/00; B32B 37/24

USPC ............ 128/200.26, 201.13, 205.24, 205.27, 128/205.29, 206.17, 207.14, 207.15, 128/207.16, 207.17, 207.18, 911, 912, 128/DIG. 26; 604/332, 333, 338, 339, 340, 604/342, 905
See application file for complete search history.

(56) References Cited

U.S. PATENT DOCUMENTS 4,582,058 A * 4/1986 Depel et al. ............. 128/207.17
4,834,732 A * 5/1989 Steer et al. .................... 604/342
(Continued)

FOREIGN PATENT DOCUMENTS

DE    690 16 228    8/2001
DE    699 20 440    10/2005
(Continued)

*Primary Examiner* — Annette Dixon
(74) *Attorney, Agent, or Firm* — Jordan and Hamburg LLP

(57) ABSTRACT

A breathing device for placing on a tracheostoma of a patient comprising a cylindrical housing, an annular housing support, a flexible flat part with sealing and adhesive functions, a filter or a speech valve, and a cover plate. The housing comprises, in the wall thereof, recesses for introducing and extracting inhaled air, and on the proximal opening thereof, an outer edge comprises at least three edge segments which are on the outer wall and at least three edge recesses. Holding rods support the filter on the proximal opening, the housing support comprises an annular flange having at least three inner wall support projections and an annular outer wall base. The support projections have a receiving area, the housing support supports the housing with the filter or speech valve into which the edge segment can be introduced in a precise manner into the support projections.

8 Claims, 3 Drawing Sheets

(56) References Cited

U.S. PATENT DOCUMENTS

Figure 1:
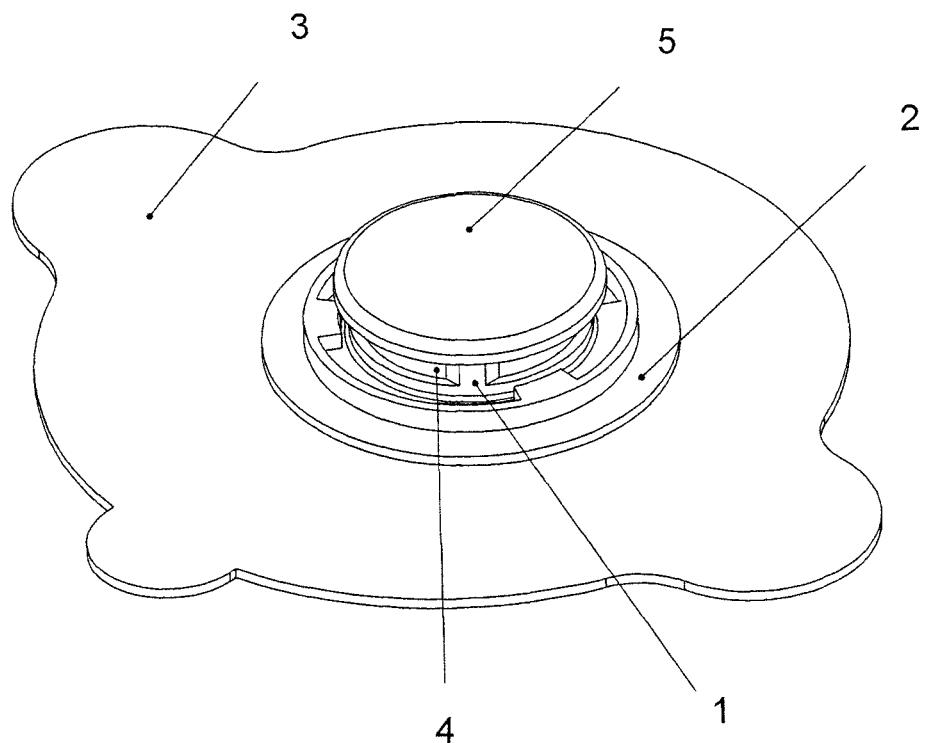

| | | | |
|---|---|---|---|
| 5,022,394 A * | 6/1991 | Chmielinski | 128/207.14 |
| 5,041,102 A * | 8/1991 | Steer et al. | 604/338 |
| 5,042,468 A | 8/1991 | Lambert | |
| 5,738,095 A * | 4/1998 | Persson | 128/207.14 |
| 6,422,235 B1 | 7/2002 | Persson | |
| 6,772,758 B2 | 8/2004 | Lambert | |
| 2003/0029456 A1 | 2/2003 | Lambert | |
| 2012/0090621 A1 * | 4/2012 | van der Houwen et al. | 128/207.16 |

FOREIGN PATENT DOCUMENTS

| | | |
|---|---|---|
| DE | 20 2008 002 602 | 8/2008 |
| DE | 20 2010 003 154 | 6/2010 |
| EP | 0 387 220 | 9/1990 |
| EP | 1 787 671 | 5/2007 |
| WO | WO-91/05579 | 5/1991 |
| WO | WO-94/19045 | 9/1994 |
| WO | WO-2009/003209 | 1/2009 |
| WO | WO-2011/144217 | 11/2011 |

\* cited by examiner

BREATHING DEVICE COMPRISING A SUPPORT FOR SPEECH VALVES AND/OR HEAT AND MOISTURE EXCHANGE DEVICES WITHOUT FIXING TO THE CANNULA

BACKGROUND OF THE INVENTION

This invention relates to a breathing device comprising a support for speech valves and/or heat and moisture exchange devices without fixing to the cannula for mounting above a tracheostoma.

Breathing devices for treating patients without larynx (laryngectomees) with opened throat (so called tracheostoma) have been known for decades.

Due to the removal of the larynx and the subsequent implant of a tracheostoma prosthesis, the communication between the nose and the lung of the laryngectomee is interrupted so that the natural function of the nose (heating, moisturizing and filtering the respiratory air as well as setting up a known respiratory resistance) is not guaranteed any more.

EP 1 787 671 A2 discloses a unit holding speech valves and/or heat and moisture exchange devices and comprising a mainly cylindrical housing, which receives the speech valve and/or the heat and moisture exchange device, and at or in the area of its proximal end the housing is inside provided with at least two projections or at least one rod into which clamps arranged in the bottom area of a retaining ring engage by rotation. In this arrangement, sealing surfaces will be formed between the proximal contact surfaces of the housing and the support surfaces of the retaining ring provided congruently to the contact surfaces, if the housing and the retaining ring are pressed against each other.

The disadvantage of this holding unit with integrated speech valve or heat and moisture exchange device is the resulting total height of the arrangement that does not lead to an optimum wear comfort for the patient. Moreover, it is complicated to open and close the internal bayonet lock so that the patient cannot enjoy an optimum ease of use.

DE 20 2008 002 602 U1 describes a unit that holds speech valves and/or heat and moisture exchange devices and comprises a mainly U-shaped receiving element that receives or clamps the speech valve and/or the heat and moisture exchange device and said U-shaped receiving element is inside provided with a U-shaped notch in which a circular bulge of an assembly part engages by being slid-in. Due to the wedge-shaped restriction of the notch in the bend, the sealing surface is pressed against the sealing edge of the assembly part so that a sealed connection is established between the sealing edge and the sealing surfaces.

This technical solution has the disadvantage that the receiving element is open towards one direction so that the direction must be observed when the unit is glued on the tracheostoma.

Furthermore, the removal of the filter element is complicated and can cause over-stretching in the throat area.

In addition to this, this technical solution does not allow a lateral air exchange.

DE 690 16 228 T3 discloses a breathing device for patients with tracheotomy comprising a support element that can be detachably connected to a respiratory hole of a patient, contains a regenerative heat and moisture exchange device and is designed as an air-proof receptacle which is provided with a first opening being connectable to the patient's respiratory hole in the throat and communicating with it then and a second opening positioned on the opposite side of the first opening and protruding from the respiratory hole to the outside. The heat and moisture exchange device provided with a filter body is mounted to the second opening by engaging into the edges of said opening in a sealed and detachable manner. In this arrangement, the distance between the first and the second opening is shorter than the dimension of the support element oriented perpendicular to it.

This heat and moisture exchange device fixed by an adhesive tape has the disadvantage that it protrudes far from the stoma when being in use. Moreover, on the upper edge of the heat and moisture exchange device a funnel-shaped supporting unit glued on the stoma is snapped in by means of claws so that it is difficult to replace the regenerative heat and moisture exchange device because it is not easy to release the clamps.

The disadvantage of this arrangement is its overall height. An additional particular disadvantage is the fact that unlocking is difficult and must be performed towards the stoma. Furthermore, this arrangement generates a high respiratory resistance due to the restriction of the cross section resulting in a less comfortable use for the patient.

SUMMARY OF THE INVENTION

The aim of the present invention is to provide a breathing device for placing on a tracheostoma of a patient that comprises a support element for speech valves and/or heat and moisture exchange devices without cannula fixation and eliminates the disadvantages of the state-of-the-art and that, in particular, does not protrude far from the stoma, ensures a good wear comfort and makes an easy replacement of filters and/or speech valves possible without involving the risk that they can be easily coughed out.

Said aim is achieved by providing a breathing device for placing on a tracheostoma according to the first claim. Advantageous embodiments of this invention are specified in the sub-claims.

The invention is based on the provision of a novel breathing device comprising a cylindrical housing, an annular housing support, a planar, movable and flexible flat part with sealing function and central hole, a filter or a speech valve, and a cover plate. Said housing contains the filter or the speech valve and is provided with a proximal opening, which can be detachably connected to the tracheostoma and is so communicating with it, and a distal opening positioned on the opposite side of the proximal opening and protruding from the tracheostoma to the outside, and the housing engages with the proximal opening in a sealed and detachable manner into the housing support that is held by the flat part over the hole and over the tracheostoma, and this arrangement is designed such that the housing comprises, in the wall thereof, recesses for introducing and extracting respiratory air, and on the proximal opening thereof, an outer edge is provided and comprises at least three edge segments on the outer wall and at least three edge recesses, said housing carries the cover plate at the distal opening and surrounds the filter, rods at the proximal opening carry the filter, the housing support comprises an annular flange with at least three support projections on the inner wall and an annular base on the outer wall, and said support projections have a receiving area that holds the housing with filter or speech valve in such a manner that the edge segments can be introduced into the support projections in a precise manner by rotating the housing in the housing support and can be locked into place in the receiving areas, and the housing support is joined to the flat part in a fixed and sealed manner.

The inventive breathing device to be placed on a tracheostoma has the advantage that it does not protrude far from the stoma, ensures a good wear comfort and makes an easy replacement of filters and/or speech valves possible without involving the risk that they can be easily coughed out.

Moreover, the inventive device has the advantage that the air exchange is performed laterally and the cross section is not restricted so that very good respiratory parameters are generated thus increasing the comfort of use for the patient.

The invention is explained in detail by means of the following embodiment and the figures.

BRIEF DESCRIPTION OF THE INVENTION

Figure 2:
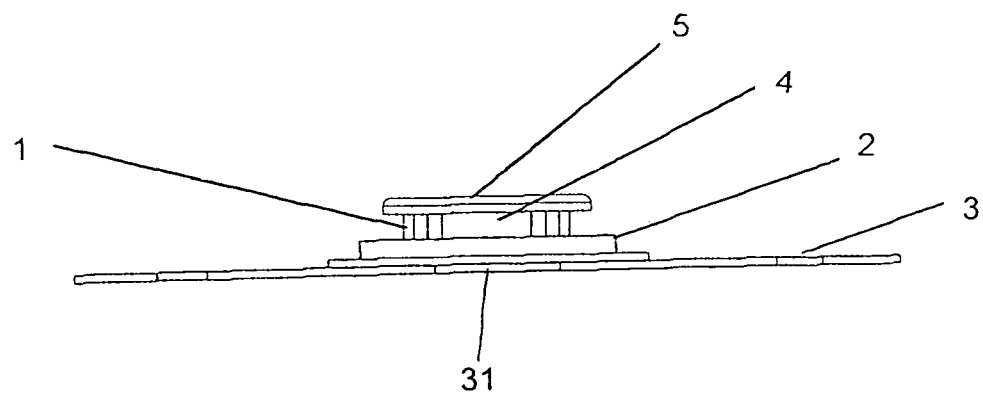
Figure 3:
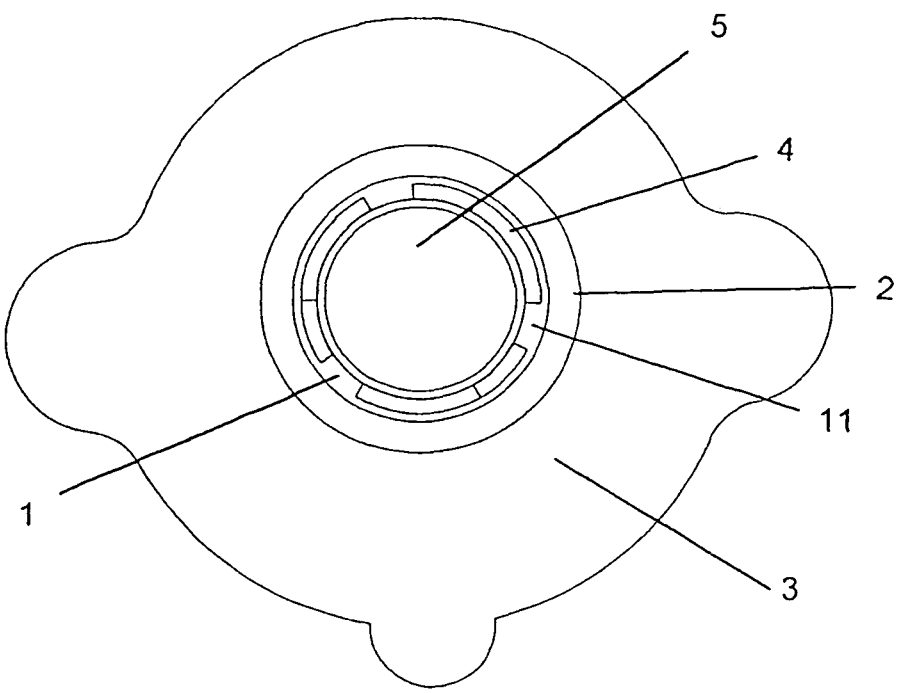
Figure 4:
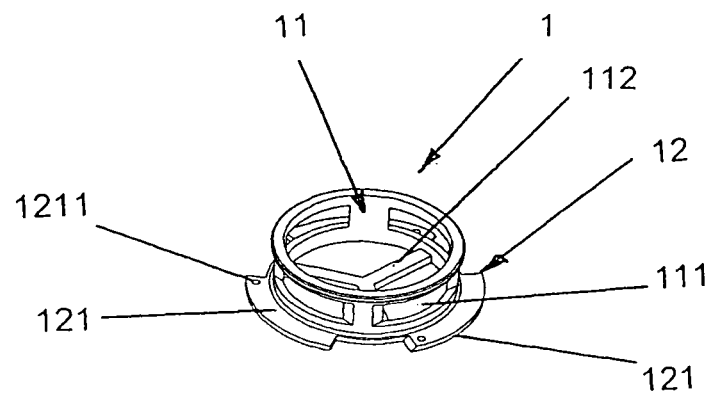
Figure 5:
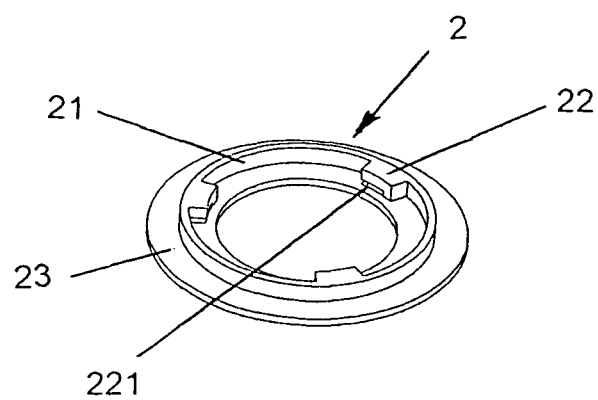

FIG. 1 is a schematic 3D view of an embodiment of an inventive breathing device, FIG. 2 is a lateral view of the breathing device according to FIG. 1, FIG. 3 is a top view of the breathing device according to FIG. 1, FIG. 4 is a schematic 3D view of the housing according to FIG. 1, and FIG. 5 is a schematic 3D view of the housing support according to FIG. 1.

DETAILED DESCRIPTION OF THE INVENTION

The breathing device for placing on a tracheostoma of a patient shown in FIG. 1 comprises a cylindrical housing (1), an annular housing support (2), a planar, movable, flexible flat part (3) with sealing function and central hole (31), a schematically illustrated conventional filter or speech valve (4) and a cover plate (5), and the housing (1) contains the filter or speech valve (4).

The housing (1) is provided with a proximal opening that can be detachably connected to the tracheostoma thus communicating with it and a distal opening positioned on the opposite side of the proximal opening and protruding from the tracheostoma to the outside, and the housing (19) engages with the proximal opening into the housing support (2) in a sealed and detachable manner.

The housing support (2) is mounted via the flat part (3) over the hole (31) and over the tracheostoma.

This device has the advantage that the wall (11) of the housing (1) is provided with recesses (111) for introducing and extracting respiratory air, that the proximal opening of the housing (1) has an outer edge (12) consisting of at least three edge segments (121) on the outer wall and at least three edge recesses, and that it carries the cover plate (5) at the distal opening simultaneously surrounding the filter or speech valve (4), and holding rods (112) support the filter or speech valve 4 on the proximal opening.

The housing support (2) comprises an annular flange (21) with at least three support projections (22) on the inner wall and an annular base (23) on the outer wall, and said support projections (22) are provided with a receiving area (221).

The housing support (2) holds the housing with filter or speech valve (4), thanks to a design in which the edge segments (121) can be introduced into the support projections (22) in a precise manner by rotating the housing (1) in the housing support (2) and can be locked in place in the receiving areas (221).

The housing support (2) is connected to the flat part (3) and the cover plate (5) in a fixed and sealed manner so that the filter or speech valve (4) or the complete housing (2) cannot be coughed out by the patient.

The connection between the housing support (2) and the cover plate (5) is detachable and can be designed, for example, as a screw or snap joint.

The connection between the housing support (2) and the flat part (3) is fixed and can be welded or glued, for example.

The edge segments (121) are advantageously provided with hemispherical locking aids (1211) on the distal side so that the connection between the support projections (22) snapped into place in the receiving areas (221) is locked and thus an easy snapping-out of the connection is prevented.

The housing support (2) is advantageously made of a soft however dimensionally stable plastic material so that it is ensured that the connection between the receiving areas (221) and the snapped-in support projections (22) cannot be detached by slight changes in shape, and simultaneously the breathing device can softly cling to the patient's throat in the area of the tracheostoma.

The flange (21) has a maximum height of 2 mm and the cover plate (5) and the flat part (3) have a maximum distance of 6 mm to each other so that the overall breathing device fits flat to the patient's throat.

The housing (1) is made of a hard plastic material, such as EVA, PS, PVC or PU. The cover plate (5) is made of a soft thermoplastic elastomer (TPE).

The flat part (3) is preferably a thin, oval foil with a thickness ranging from 30 µm to 0.9 mm. It is made of silicone or an elastomer (e.g. TPU, TPE or TPS) or of hydrocolloid.

The housing support (2) is placed centrally above the tracheostoma of the patient by means of the flat part (3). The flat part (3) is provided with an adhesive function at the proximal side so that in this position, surrounding the tracheostoma, it can be glued to the patient's skin in a sealed manner thus allowing the air to pass from the tracheostoma through the hole (31) into the housing (1). From the housing (1) the air can circulate via the recesses (11) through the filter or speech valve (4) so that respiratory air can be inhaled and exhaled.

All features disclosed in the description, the embodiments and the subsequent claims can be important for the invention both individually and in any combination.

The invention claimed is:

1. A breathing device for placing on a tracheostoma of a patient comprising:
   a cylindrical housing;
   an annular housing support;
   a plane, movable, flexible flat part with sealing and adhesive functions and central hole;
   a filter or a speech valve; and
   a cover plate;
   and wherein the housing contains the filter or the speech valve and is provided with a proximal opening that is detachably connected to the tracheostoma thus communicating with it, and a distal opening positioned at an opening side opposite to the proximal opening and protruding from the tracheostoma to the outside, and the housing engages with the proximal opening into the housing support in a sealed and detachable manner and is mounted via the flat part above the hole and the tracheostoma, wherein
      the housing comprises, in the wall thereof, recesses for introducing and extracting respiratory air, and on the proximal opening thereof, an outer edge comprises at least three edge segments which are on the outer wall and at least three edge recesses, said housing carries the cover plate at the distal opening of the housing and surrounds the filter or the speech valve, and holding rods hold the filter on the proximal opening;
      the housing support comprises an annular flange having at least three inner wall support projections and an annular outer wall base and said support projections are provided with a receiving area;

the housing support supports the housing with filter or speech valve by a configuration in which the edge segments can be precisely engaged into the support projections by rotating the housing in the housing support and can be locked in place in the receiving areas; and the housing support is joined to the flat part in a fixed and sealed manner.

2. The breathing device according to claim 1, wherein the edge segments are provided with locking aids on the distal side.

3. The breathing device according to claim 1, wherein the housing support and the flat part are welded or glued with each other.

4. The breathing device according to claim 1, wherein the housing support is made of a soft, dimensionally stable plastic material.

5. The breathing device according to claim 1, wherein the flange has a maximum height of 2 mm and the cover plate and the flat part are arranged at a maximum distance of 6 mm to each other.

6. The breathing device according to claim 1, wherein the housing is made of a hard plastic material and the cover plate is made of a soft thermoplastic elastomer.

7. The breathing device according to claim 1, wherein the flat part is a thin, oval foil with a thickness ranging from 30 μM to 0.9 mm and is made of silicone or an elastomer.

8. The breathing device according to claim 1, wherein at the proximal side the flat segment is provided with an adhesive function.

\* \* \* \* \*